(12) United States Patent
Berry (10) Patent No.: US 7,993,340 B2
(45) Date of Patent: Aug. 9, 2011

(54) INSTRUMENTS AND TECHNIQUES FOR SPINAL DISC SPACE PREPARATION

(75) Inventor: Bret M. Berry, Cordova, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 1114 days.

(21) Appl. No.: 11/455,453

(22) Filed: Jun. 19, 2006

(65) Prior Publication Data

US 2006/0247654 A1 Nov. 2, 2006

Related U.S. Application Data

(62) Division of application No. 10/186,082, filed on Jun. 28, 2002, now Pat. No. 7,083,625.

(51) Int. Cl.
*A61B 17/00* (2006.01)
(52) U.S. Cl. ............................................. 606/79
(58) Field of Classification Search .............. 606/79, 606/80, 86 R, 87, 96, 279; 144/371, 372
See application file for complete search history.

(56) References Cited

U.S. PATENT DOCUMENTS

| | | | | |
|---|---|---|---|---|
| 4,319,615 A * | 3/1982 | Ditmanson | | 144/144.1 |
| 4,586,496 A | 5/1986 | Keller | | |
| 4,697,586 A | 10/1987 | Gazale | | |
| 5,207,680 A | 5/1993 | Dietz et al. | | |
| 5,484,437 A * | 1/1996 | Michelson | | 606/86 A |
| 5,484,446 A | 1/1996 | Burke et al. | | |
| 5,486,180 A | 1/1996 | Dietz et al. | | |
| 5,540,695 A | 7/1996 | Levy | | |
| 5,571,109 A | 11/1996 | Bertagnoli | | |
| 5,601,563 A | 2/1997 | Burke et al. | | |
| 5,688,281 A | 11/1997 | Cripe et al. | | |
| 5,772,661 A | 6/1998 | Michelson | | |
| 5,803,904 A | 9/1998 | Mehdizadeh | | |
| 5,899,908 A * | 5/1999 | Kuslich et al. | | 606/96 |
| 6,159,214 A | 12/2000 | Michelson | | |
| 6,224,599 B1 | 5/2001 | Baynham et al. | | |
| 6,764,491 B2 * | 7/2004 | Frey et al. | | 606/85 |
| 7,033,362 B2 * | 4/2006 | McGahan et al. | | 606/96 |
| 2002/0058944 A1 * | 5/2002 | Michelson | | 606/79 |

FOREIGN PATENT DOCUMENTS

| | | |
|---|---|---|
| DE | 201 1 479 U1 | 8/2001 |
| WO | WO 98/04202 A1 | 2/1998 |
| WO | WO 99/52446 A2 | 10/1999 |
| WO | WO 99/52453 A2 | 10/1999 |
| WO | WO 01/28435 A1 | 4/2001 |
| WO | WO 01/62166 A2 | 8/2001 |
| WO | WO 02/03867 A2 | 1/2002 |
| WO | WO 02/09606 A2 | 2/2002 |

* cited by examiner

*Primary Examiner* — Thomas C. Barrett
*Assistant Examiner* — David W Bates (57) ABSTRACT

A milling instrument assembly is provided for vertebral endplate preparation along a cutting path obliquely oriented to the axis of approach to the vertebra. The milling instrument assembly provides control of the anterior-posterior depth of endplate removal by guiding cutting assembly in the disc space as it moves transversely across a housing assembly. Methods and techniques are included for using the milling instrument assembly in spinal surgery.

15 Claims, 9 Drawing Sheets

INSTRUMENTS AND TECHNIQUES FOR SPINAL DISC SPACE PREPARATION

CROSS-REFERENCE TO RELATED APPLICATION

The present application is a divisional of U.S. patent application Ser. No. 10/186,082 filed on Jun. 28, 2002 now U.S. Pat. No. 7,083,625, which is incorporated herein by reference.

BACKGROUND

Implants of various types have been utilized throughout the body for various orthopedic bone applications, including application in the field of preparing an intervertebral disc space to receive an interbody fusion device to create bony fusion or a spacer providing artificial disc functions. Such procedures may be necessary where the natural disc has degenerated or slipped resulting in pain and discomfort to a patient. The deterioration or movement of the disc often results in the two adjacent vertebral bodies coming closer together. A common treatment is to surgically restore the proper disc space height to thereby alleviate the neurologic impact of the collapsed disc space. Typically, the damaged disc is removed and a load bearing structure, either man-made or natural, is inserted to maintain the disc height and promote bony fusion and/or restore motion between the adjacent vertebrae.

Prior instruments and techniques for disc space preparation have been provided to prepare a disc space for insertion of an interbody implant. For example, milling devices have been provided to remove bone from a vertebral endplate. Milling devices can intrude on the other anatomical structures of the vertebra other than the endplate, such as the posterior elements of the vertebra where the spinal cord is located. There remains a need for instruments that reduce intrusion on the anatomical structures of the vertebra other than the endplate during preparation of the disc space for receipt of an implant.

SUMMARY

The present invention relates generally to instruments and techniques for preparing a site between two adjacent bony segments from an anterior oblique approach to receive an implant therebetween. The present invention further relates generally to instruments and techniques for vertebral endplate preparation along a path obliquely oriented to the axis of approach to the vertebra.

In one aspect of the invention, an instrument is provided that includes a housing positionable adjacent the spinal disc space. The instrument includes a block proximal the housing. A cutting assembly extends through the block and into the housing. When inserted, the instrument has a longitudinal axis extendable from the spinal column. The cutting assembly is guidable with the block along a cutting path extending transversely to the longitudinal axis. At least a portion of the cutting path extends obliquely to the longitudinal axis.

Another aspect of the invention contemplates an instrument having a housing assembly positionable adjacent a vertebra. The instrument includes a cutting assembly extendable through the housing assembly. When positioned adjacent the vertebra, the instrument includes a longitudinal axis extending from the spinal column. The cutting assembly is guidable along a guide surface of the housing assembly. The guide surface extends transversely to the longitudinal axis. At least a portion of said guide surface extends obliquely to the longitudinal axis.

In a further aspect of the invention, an instrument includes a housing assembly positionable adjacent a vertebra. The instrument includes a cutting assembly extending through the housing assembly. The instrument includes a longitudinal axis extending from the spinal column when the housing assembly is positioned adjacent the vertebra. The instrument includes means for guiding the cutting assembly relative to the housing assembly along a cutting path. At least a portion of the cutting path extends obliquely relative to the longitudinal axis.

The invention further contemplates a method of disc space and endplate preparation from an anterior oblique approach to the spine. In one aspect, the method includes gaining access to the spine and inserting a cutting assembly into the spinal disc space from an anterior oblique approach. The method includes guiding the cutting of one or both of the endplates along a cutting path having a first portion extending orthogonally to the direction of the approach and another portion obliquely oriented to the direction of the approach.

In another aspect, the method includes gaining access to and inserting a cutting assembly into the spinal disc space from an anterior oblique approach. The method also includes guiding the cutting of one or both of the endplates along a cutting path in the disc space, at least a portion of which extends obliquely to the angle of approach to the disc space.

These and other aspects will also become apparent from a review of the accompanying drawings and descriptions thereof.

DESCRIPTION OF THE ILLUSTRATED EMBODIMENTS

For the purposes of promoting an understanding of the principles of the invention, reference will now be made to the embodiments illustrated in the drawings and specific language will be used to describe the same. It will nevertheless be understood that no limitation of the scope of the invention is thereby intended. Any such alterations and further modifications in the illustrated device, and any such further applications of the principles of the invention as illustrated herein, are contemplated as would normally occur to one skilled in the art to which the invention relates.

The present invention relates to instruments and methods for gaining access to a disc space between adjacent vertebral bodies, distracting the disc space to a desired height, preparing the disc space to receive an implant to maintain disc space height and angulation, and a method for inserting an implant into the prepared disc space. More specifically, while methods and instruments disclosed in the present application may have application in other areas of the spine or the body, it is specifically contemplated that the present instruments and methods may be utilized in preparation of an obliquely oriented site on an endplate of a vertebra. An anterior-oblique approach to the spine may be desirable in certain areas of the spine where a direct anterior approach is difficult or impossible because of patient anatomy. Other approaches, including direct anterior and lateral approaches, are also contemplated. The term implants in the present application is used in a broad sense to encompass both implants constructed of man-made materials, as well as implants formed of naturally occurring materials. Further, implants contemplated to be used with the present invention may include those intended to promote fusion between adjacent vertebra as well as artificial disc replacements.

Figure 1:
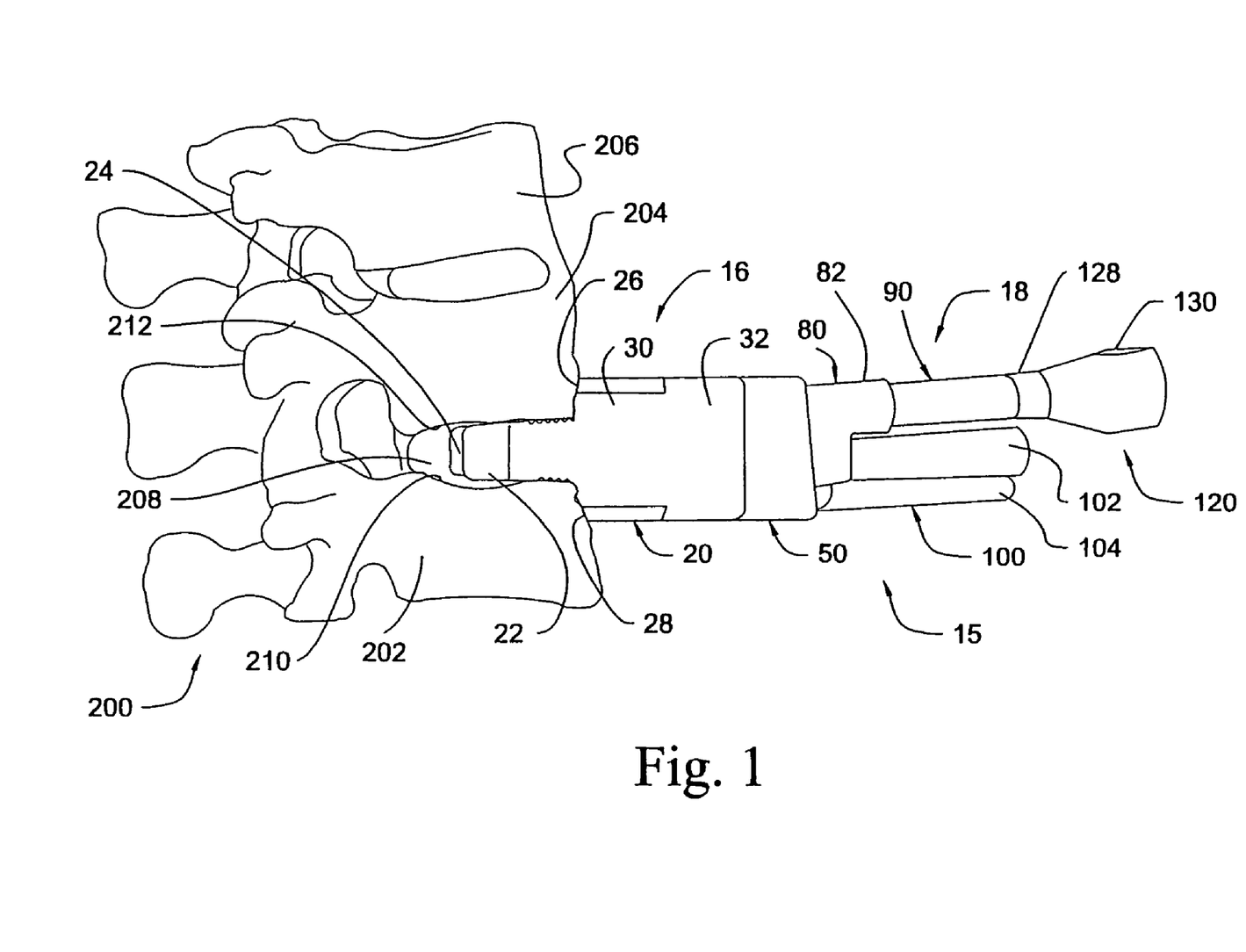
FIG. 1 is a side view of a spinal column segment and a milling instrument assembly positioned adjacent thereto in an anterior oblique approach.
Figure 2:
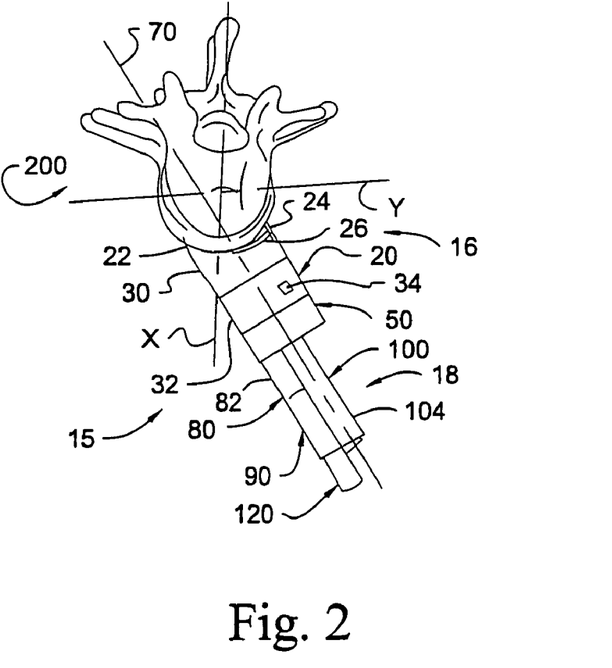
FIG. 2 is a plan view of the spinal column segment and milling instrument assembly of FIG. 1.
Figure 3:
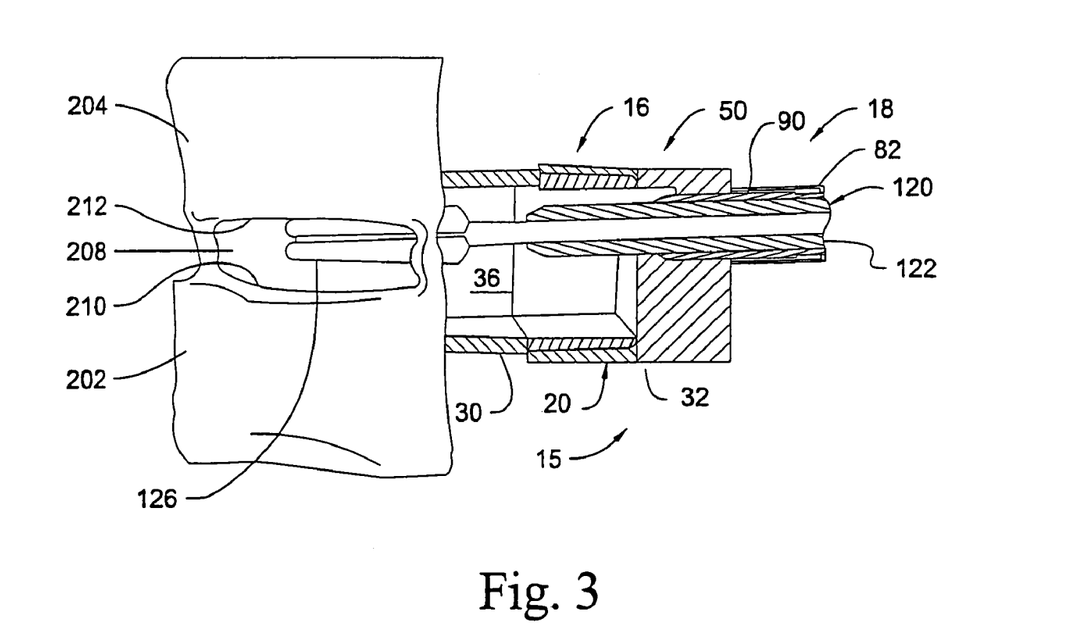
FIG. 3 is a sectional view looking at the side of the spinal column segment and milling instrument assembly of FIG. 1.
Figure 6:
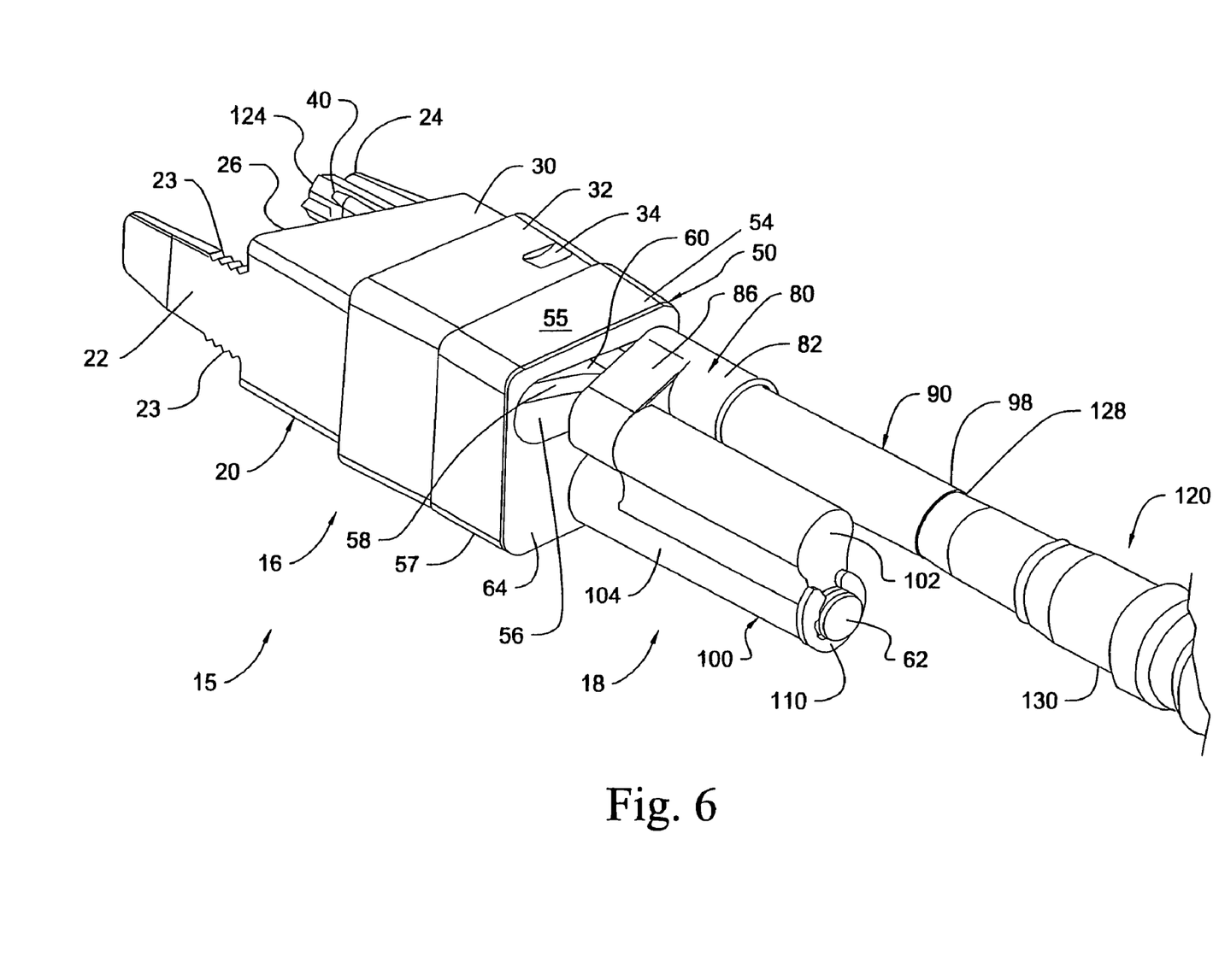
FIG. 6 is a perspective view of the milling instrument assembly.
Figure 7:
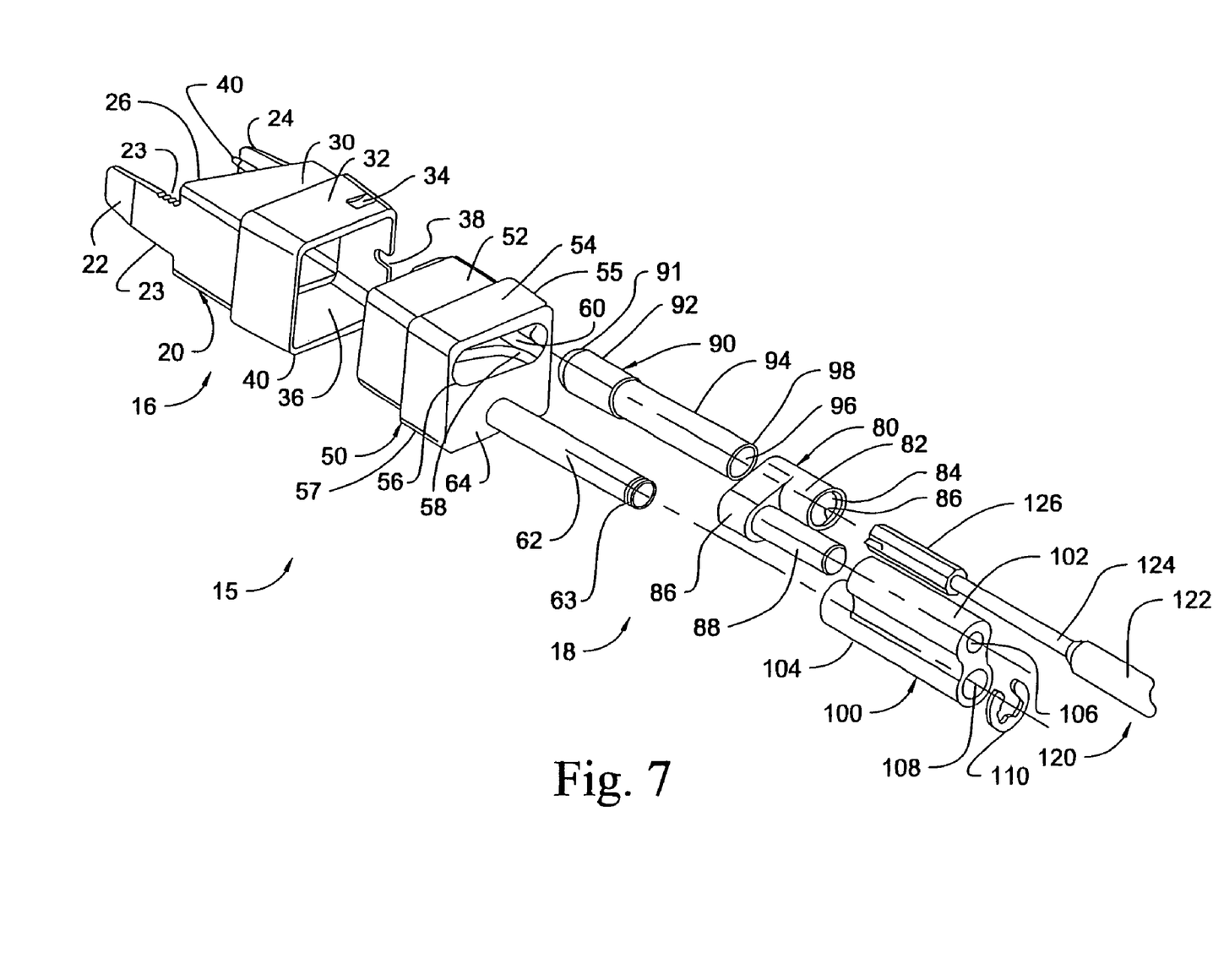
FIG. 7 is an exploded perspective view of the milling instrument assembly of FIG. 6.

Referring to FIG. 1, there is shown a milling instrument assembly 15 positioned adjacent spinal column segment 200. Milling instrument assembly 15 can be positioned adjacent the disc space of adjacent vertebrae in a patient, and used by the surgeon to prepare one or both of the endplates of the adjacent vertebrae to receive an implant. Referring further to FIGS. 2-3, and as also shown in FIGS. 6 and 7, milling instrument assembly 15 includes a housing assembly 16 at its distal end positionable adjacent disc space 208. Milling instrument assembly 15 also includes a guide assembly 18 extending proximally from housing assembly 16. Guide assembly 18 extends between and is coupled with a cutting assembly 120 and with housing assembly 16. Cutting assembly 120 extends through housing assembly 16 and into disc space 208.

Figure 4:
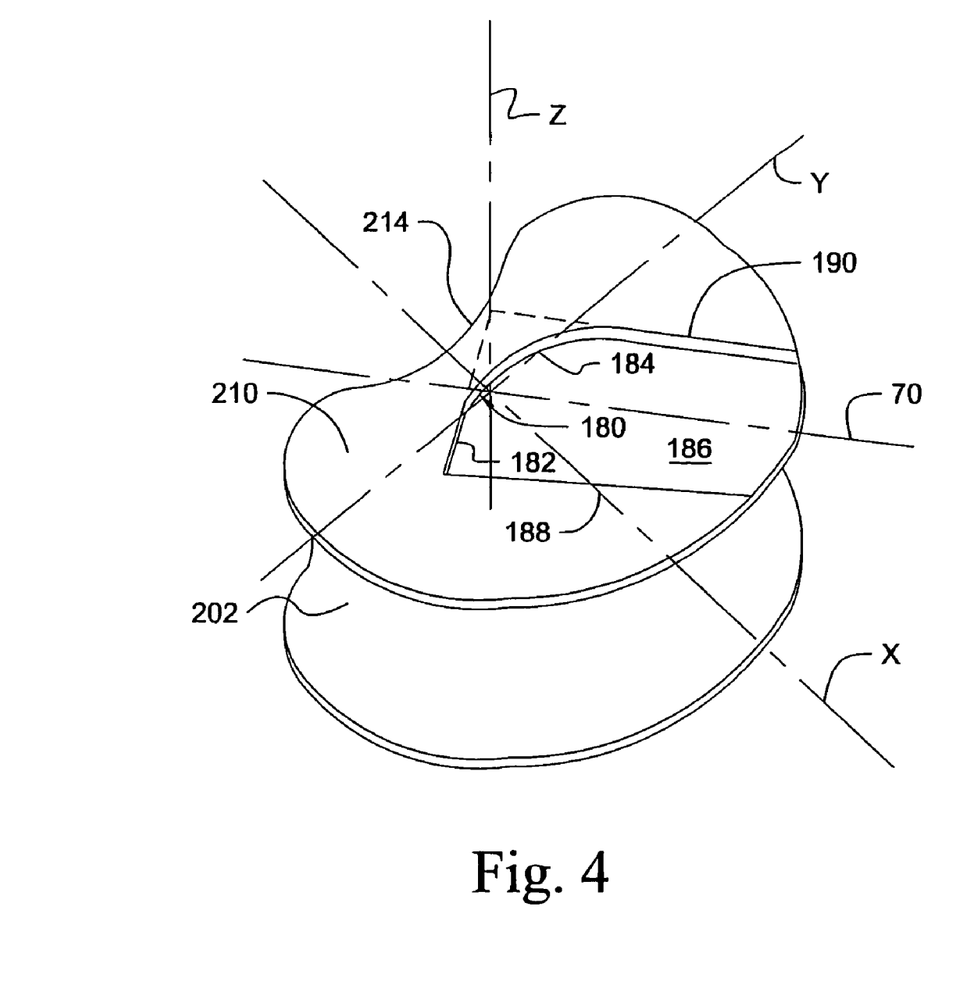
FIG. 4 is a perspective view of a vertebral body showing a milling pattern in an endplate thereof provided by the milling instrument assembly of FIG. 1.

There is shown a spinal column segment 200 including vertebrae 202, 204, and 206. Disc space 208 is between vertebrae 202 and 204. Vertebra 202 has endplate 210, and vertebra 204 has endplate 212. Access to disc space 208 is obtained by any known surgical technique and will not be described in detail herein. With respect to the view of FIGS. 2 and 4, the X axis represents the anterior to posterior direction, the Y axis extends laterally, while the Z axis extends in the superior to inferior direction. As shown in FIGS. 2 and 4, milling instrument assembly 15 has a longitudinal axis 70 that, when inserted for an anterior oblique approach to the disc space, extends obliquely to the X axis and also to the Y axis. Stated another way, the position of longitudinal axis 70 can be obliquely oriented to the sagittal plane (X axis) and coronal plane (Y axis) of the patient.

Housing assembly 16 includes a housing 20 and a block 50 removably mounted in the proximal end of housing 20. Housing 20 includes a distal portion 30 and a proximal portion 32. Proximal portion 32 can include a recess 34 to facilitate attachment of other instruments, such as a guide tube, to housing 20. Block 50 is attached to proximal portion 32. A passage or working channel 36 (FIG. 3) extends through housing 20, and extensions 22, 24 extend distally from distal portion 30 on either side of the passage or working channel 36. Housing 20 can include upper arcuate distal end surface 26 and lower arcuate distal end surface 28 each adapted to contact or extend generally along the arcuate anterior oblique surfaces of the adjacent vertebra 204, 202 on either side of disc space 208.

Housing 20 can be provided with extensions 22, 24 extending distally therefrom adapted and configured to extend into disc space 208. Extensions 22 and 24 can each engage the endplates 210, 212 to maintain the distraction obtained with a previously inserted distractor. It is also contemplated that extensions 22, 24 can be self-distracting. It is further contemplated that extensions 22, 24 can be non-distracting. Each of the extensions 22, 24 can be provided with an external taper on its leading surface adapted to urge tissue to the exterior of the housing and away from the distal end opening of housing 20. Extensions 22, 24 can also include bone engaging surfaces 23 that bite into or grip the adjacent vertebral endplate to inhibit dislodgment once positioned in disc space. Housing 20 retains its position in the disc space and adjacent the anterior portions of vertebrae 204 and 206 with extensions 22 and 24 engaging end plates 210 and 212 to maintain the disc space height and angulation established thereby or by previous distraction. Extension 22 can have a greater length than extension 24 for extension to a greater depth in disc space 208, with each extension 22, 24 having a length corresponding to the depth of cut to be made adjacent thereto.

Cutting assembly 120 includes a shaft 122 extending through a depth tube 90. Cutting assembly 120 includes a proximal portion 130 proximal depth tube 90 and a cutting element 126 in disc space D. Cutting assembly 120 can be engaged with depth tube 90 by, for example, abutting enlarged shaft portion 128 against the proximal end of depth tube 90. When so engaged, cutting assembly 120 is not movable axially in the distal direction in depth tube 90. Depth tube 90 abuttingly engages block 50 and moves along a guide surface extending across block 50, providing a controlled depth of cut in the proximal-distal direction in disc space 208 for cutting element 126. To facilitate movement of depth tube 90 across block 50, a linkage 80 extends around depth tube 90. Linkage 80 is coupled to a first connecting member 102 of guide housing 100. Guide housing 100 includes a second connecting member 104 coupled to block 50. Linkage 80 and guide housing 100 move with depth tube 90 across block 50 while maintaining cutting assembly 120 in parallel alignment with axis 70.

Referring now to FIG. 4, depth tube 90, and thus cutting assembly 120, are guided across block 50 to provide a prepared endplate site 186 formed by moving cutting element 126 along a length of a cutting path 180 between a first side 188 and a second side 190 of prepared site 186. In FIG. 4, the endplate 210 of lower vertebra 202 is shown, it being understood that endplate 212 of vertebra 204 would have a substantially similar shape formed by the cutting element 126 positioned as shown in FIG. 3. Cutting path 180 includes a first portion 182 extending orthogonally to longitudinal axis 70 of milling instrument assembly 15. Cutting path 180 further includes a second portion 184 that extends obliquely to longitudinal axis 70.

In the illustrated embodiment, oblique second portion 184 is curved or arcuate between first portion 182 and a second side 190. The oblique second portion 184 can comprise about one half the length of cutting path 180. It is contemplated that oblique portion 184 can range from the entire length of cutting path 180 to about one-eighth of the length of cutting path 180 or less. In another form, the oblique portion comprises one-fourth to three fourths of the length of cutting path 180. It is also contemplated that second portion 184 can be linear, or a combination of linear and curved segments. It is further contemplated that the entire cutting path 180 can be obliquely oriented relative to longitudinal axis 70.

Cutting path 180 is formed by moving cutting assembly 120 side-to-side along across block 50 transversely to longitudinal axis 70. This moves cutting element 126 in the disc space along the adjacent vertebral endplate. Prepared site 186 has a first side 188 that has a greater length than a second side 190. This shorter second side 190 is formed by moving cutting element proximally as it is guided between first side 188 and second side 190. In this manner, cutting element 126 is moved away from posterior elements of the vertebra, such as posterior side 214 of vertebra 202. If cutting path 180 were entirely orthogonal to longitudinal axis 70, the extension of the cutting element into disc space 208 along first side 188 would have to be reduced to avoid posterior side 214 of vertebra 202, or the possible intrusion into the posterior elements with cutting element 126 would have to be tolerated. Accordingly, milling instrument assembly 15 allows cutting element 126 to extend far into disc space 208 along first side 188, while cutting element 126 is moved away from the posterior elements of vertebra 214 as cutting element 126 is guided toward second side 190.

It is contemplated that housing 20 can then provide an access port or window into disc space 208. It is also contemplate that a guide or retractor tube could be attached to housing 20 to facilitate disc space preparation and/or implant insertion into disc space 208. For example, block 50, guide assembly 18 and cutting assembly 120 could be positioned in a guide tube during endplate preparation. After endplate preparation, block 50, guide assembly 18 and cutting assembly 120 could be removed and the guide tube used to access the prepared disc space.

Figure 5:
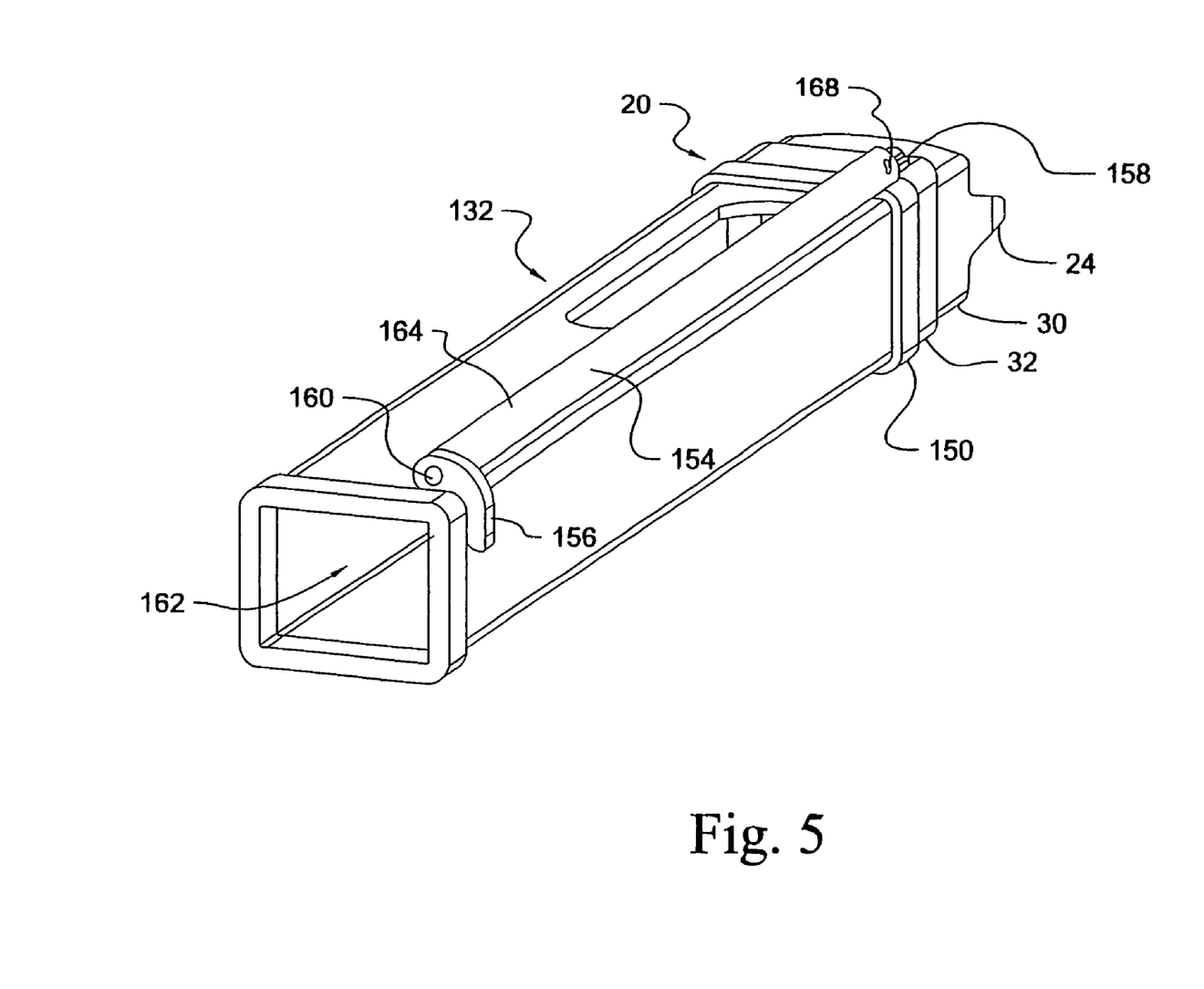
FIG. 5 is a perspective view of a guard tube attached to a housing of the milling instrument assembly of FIG. 1.

In FIG. 5 there is one embodiment of a guide tube 132 that is provided with a substantially rectangular or square working channel 162 adapted and configured to correspond with the proximal dimensions of housing 20. Also contemplated are guide tubes having working channels with substantially circular, oval, figure-eight or any other cross-sectional configurations that may be utilized for disc space preparation and implant insertion. Guide tube 132 can be provided with a front flange 150 adapted to engage the proximal portion of housing 20. Guide tube 132 also includes retaining assembly 154 that may be utilized to selectively couple guide tube 132 to housing 20. Retaining assembly 154 includes an outer shaft 164 coupled to guide tube 132. An inner shaft 160 extends along the length of outer tube 164. A finger lever 156 is positioned at the proximal end of inner shaft 160, and a retaining foot 158 is positioned at or near the distal portion of inner shaft 160.

Housing 20 may be coupled to guide tube 132 by initially bringing guide tube 132 into a butting engagement with housing 20 such that flange 150 surrounds at least a portion of housing 20. Lever 156 may then be rotated to cause retaining foot 158 to rotate into recess 34 on housing 20. With retaining foot 168 extending into recess 34, housing 20 and guide tube 132 are removably coupled to one another. Guide tube 132 and housing 20 may then be advanced over any inserted distractor or guided into position into the disc space with a centering element or the like. The proximal end of guide tube 132 can be impacted or driven toward the disc space to advance distraction holders 22 and 24 into the disc space. Once the guide tube and/or housing 20 have been properly positioned, any inserted distractor or other instrument can be removed from the disc space leaving the guide tube and housing assembly in place. When desired to remove guide tube 132, lever 156 of retaining assembly 154 may then be rotated in an upward direction thereby causing retaining foot 158 to rotate out of recess 34 of housing 20. With retaining foot 158 positioned out of engagement with recess 34, guide tube 132 may be disengaged from housing 20.

Referring to FIGS. 6 and 7, there are shown further details of milling instrument assembly 15. Housing assembly 16 includes housing 20 and block 50 removably mounted in the proximal end of housing 20. Housing 20 includes distal portion 30 and proximal portion 32 having working channel or passage 36 extending therethrough. Extensions 22, 24 extend distally from distal portion 30 on either side of passage 36. A projection or spike 40 can extend distally from one or both of the distal end surfaces 26, 28 for engagement with the adjacent vertebral body.

Passage 36 can be sized in proximal portion 32 to receive a distal portion 52 of block 50 therein so that block 50 abuts against proximal end 40 of housing 20. Proximal portion 54 of block 50 resides proximally of housing 20. Distal portion 52 can provide a substantially close fit with the internal dimensions of proximal portion 32 of housing 20 such that block 50 is not movable with respect to the housing 20 in directions other than proximally toward the user. It is contemplated that block 50 can be removably attached to housing 20 before and/or after housing 20 has been positioned adjacent the spinal disc space. Block 50 can be attached with a friction or interference fit with housing 20, or via one or more coupling mechanisms, such as a clip, fastener, ball-detent mechanism or other coupling mechanism. Other embodiments contemplate that block 50 can be integral with housing 20.

It is further contemplated that housing 20 can be provided with an indicator receptacle 38 to receive indicator 51 (FIG. 8) of block 50 when block 50 is properly positioned in housing 22. In this manner, the surgeon is provided an indication of whether cutting assembly 120 is positioned along the appropriate vertebral endplate since indicator 51 will contact the proximal end of housing 20 and prevent proper seating of block 50 therein unless indicator 51 is received in receptacle 38. For example, the illustrated embodiment shows a block 50 configured for positioning cutting assembly 120 along the upper vertebral endplate. A second block could be provided for attachment to housing 20 and configured for positioning cutting assembly 120 along the lower vertebral endplate. The first and second blocks would not properly seat on housing 20 unless indicator 51 was received in receptacle 38, orienting the cutting element along the appropriate upper or lower vertebral endplate.

Figure 9:
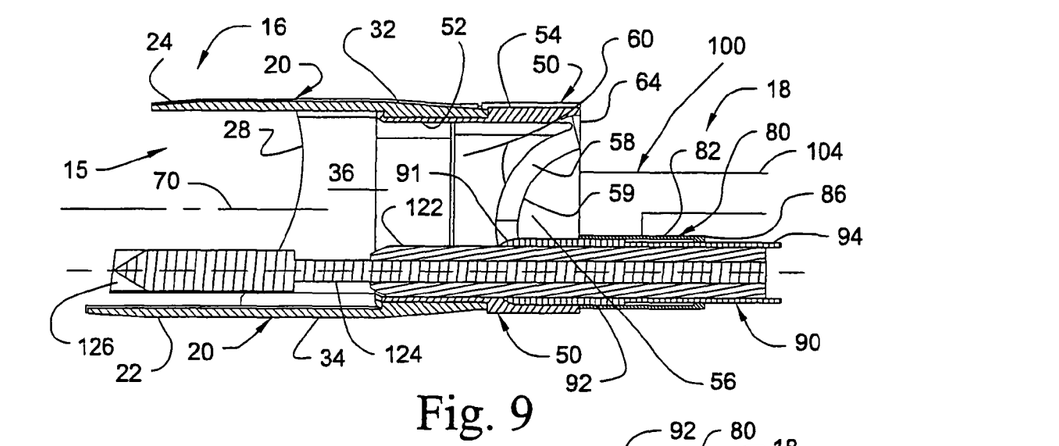
FIG. 9 is a section view through line 9-9 of FIG. 8 with the cutting assembly of the milling instrument assembly in a first position.

Block 50 includes a proximal face 64 having a slot 56 formed therein. Slot 56 includes a through-way 60 extending therethrough in communication with passage 36. A guide surface 58 extends about through-way 60, and, as discussed further below, forms a guide surface along which cutting assembly 120 is guided with guide assembly 18 for endplate preparation along cutting path 180. It is further contemplated that slot 56 of block 50 can be configured for preparing the vertebral endplates in a manner that establishes and/or maintain angulation between adjacent vertebra relative to the axial plane. For example, as shown in FIG. 9, upper surface 72 and lower surface 74 of slot 56 can be disposed at an angle 68 with respect to the longitudinal axis 70 of housing assembly 16. In the illustrated embodiment, longitudinal axis 70 extends parallel to the axial plane of the patient.

Instrument assembly 15 further includes guide assembly 18 adapted to guide cutting assembly 120 across housing assembly 16 during endplate preparation. Guide assembly 18 includes a guide housing 100 mountable on mounting post 62 and a linkage 80 extending between and coupling guide housing 100 with cutting assembly 120. Linkage 80 includes a guide tube 82 having a passage 84 extending therethrough. A connecting portion 86 extends between and connects linkage post 88 with guide tube 82. Connecting portion 86 can be integrally formed with guide tube 82 and linkage post 88, although separable and/or rigidly attached components are also contemplated for linkage 80.

Guide housing 100 includes a first connecting member 102 and a second connecting member 104. First connecting member 102 includes a passage 106 sized to receive linkage post 88 of linkage 80 therein, and second connecting member 104 includes a passage 108 sized to receive mounting post 62 of block 50 therethrough. First and second connecting members 102, 104 extend alongside one another, and can be integrally formed with one another or separable but rigidly attached components. When assembled, first connecting member 102 is adjacent connecting portion 86 of linkage 80 and second connecting member 104 is adjacent proximal face 64 of block 50. A fastener 110 is engageable in recess 63 extending about mounting post 62 to secure guide housing 100 to mounting post 62. Fastener 110 can be a snap ring, crimpable ring, cotterpin, or other fastener capable of securing mounting post 62 to guide housing 100.

Figure 8:
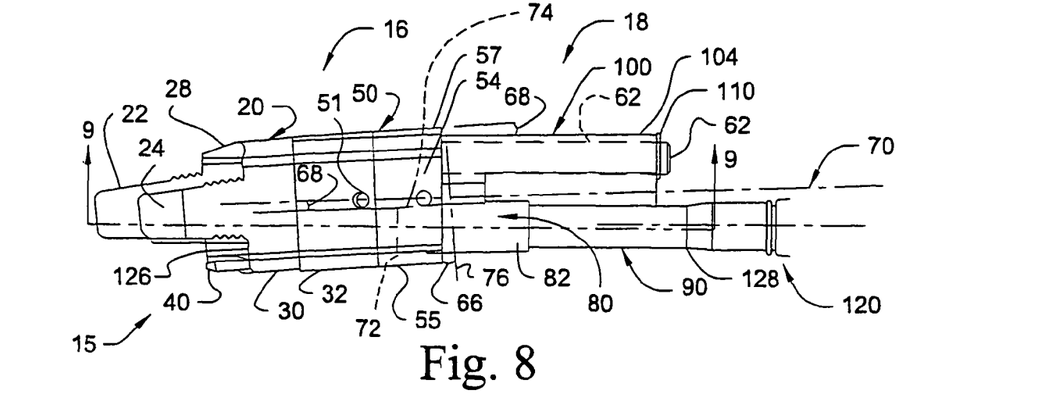
FIG. 8 is a side elevation view of the milling instrument assembly of FIG. 6 rotated 180 degrees about its central axis so that it is upside down relative to FIG. 6.

It is contemplated block 50 can be angled with respect to the longitudinal axis 70 to permit end plate cutting and preparation at an angle desirable to maintain and/or establish an angular relationship between adjacent vertebrae. For example, as shown in FIG. 8, proximal face 64 can be set at a corresponding angle 66 with respect to an axis 76 extending orthogonally to longitudinal axis 70. It will be understood that the angulation of proximal face 64 provides proximal portion 54 with a taper from bottom surface 57 to a lesser thickness at upper surface 55. Thus, proximal face 64 can provide a reference plane for the attachment of other guiding elements such that they may be maintained in the proper angular relationship with the angle of slot 56. It is further contemplated that mounting post 62 can be centrally located between the sidewalls of distal portion 54 below slot 56, and extend from proximal face 64 at angle 68 relative to longitudinal axis 70. It is also contemplated that upper and lower surfaces 72, 74 for slot 56 and/or mounting port 62 can extend substantially parallel to longitudinal axis 70.

Guide assembly 18 further includes depth tube 90. Depth tube 90 includes a passage 96 sized to receive at least a portion of cutting assembly 120 therein. The proximal end 98 of depth tube 90 can contact an enlarged portion 128 along shaft 122 of cutting assembly 120 to limit distal movement of cutting assembly 120 relative to depth tube 90. Depth tube 90 includes a distal end 91 and an enlarged distal portion 92 residing within slot 56 and a proximal portion 94 between enlarged distal portion 92 and proximal end 98. Distal end 91 can be chamfered, tapered or have a spherical shape to reside in abutting engagement with a correspondingly shaped guide surface 58 extending around through-way 60. Depth tube 90 extends through guide tube 82 of linkage 80. Guide tube portion 82 includes an internal lip 86 extending radially into passage 84. Lip 86 is engageable with enlarged portion 92 to limit proximal movement of depth tube 90 in guide tube 82.

Guide assembly 18 is assembled by placing guide tube 82 around depth tube 90 and depth tube 90 around the shaft of cutting assembly 120. First connecting member 102 of guide housing 100 is positioned over linkage post 84 of linkage 80. Second connecting member 104 is placed over mounting post 62 with distal end 91 of depth tube 90 positioned in slot 156. Cutting element 126 can be mounted on distal portion 124 of shaft 122 extending into passage 36, and fastener 110 placed around the proximal end of mounting post 62 to secure guide housing 100. Alternatively, if cutting element 126 were integral with shaft 122, proximal portion 130 can be attached to shaft 122 after insertion of shaft 122 proximally through the distal ends of housing assembly 16 and depth tube 90.

Guide housing 100 is rotatable about mounting post 62 and linkage post 84, and guide tube 82 is rotatable about depth tube 90. This interconnection between block 50 and cutting assembly 120 permits movement of depth tube 90 along slot 56 with its distal end 91 in abutting engagement with guide surface 58. As shown in FIG. 8, depth tube 90 and guide tube portion 82 can be disposed at an angle 68 with respect to the longitudinal axis 70 of milling instrument assembly 15. Thus, depth tube 90 is in substantial alignment with the upper and lower surfaces 72, 74 of slot 56 and will be maintained in substantial alignment throughout the cutting process. Enlarged distal portion 92 can snugly fit within slot 56 to provide precise guiding of the cutting element 126 along guide surface 58 and limit or prevent movement of cutting element 126 relative to the axial plane or in the direction of the Z axis. As shown in FIGS. 9-12, distal end 91 of depth tube 90 engages guide surface 58 of slot 56 to limit the distal axial extent cutting element 126 may extend within passage 36. Furthermore, enlarged portion 128 of shaft 122 abuts the proximal end 98 of depth tube 90 to limit the distal axial extent cutting element 126 can move relative to depth tube 90.

Guide assembly 18 and block 50 may be coupled with housing 20 so that cutting element 126 extends into passage 36 between extensions 22, 24. Cutting element 126 can be a burr with a cutting bit configured to engage and cut exposed vertebral bone or other tissues of the adjacent vertebral endplate with reciprocating or rotational motion as it is moved along guide surface 58. It is contemplated that proximal portion 130 can include a handle and/or a coupler for attachment to a power source to drive cutting element 126. Other cutting elements and drive means are also contemplated, including hand operated instruments, may be utilized in combination with housing assembly 16 and guide assembly 18.

Figure 10:
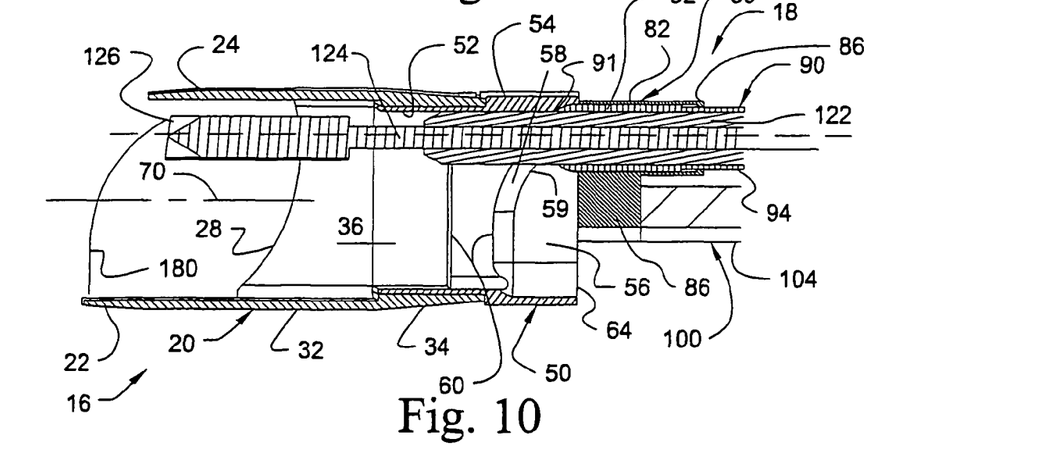
FIG. 10 is the section view of FIG. 9 with the cutting assembly in a second position.
Figure 11:
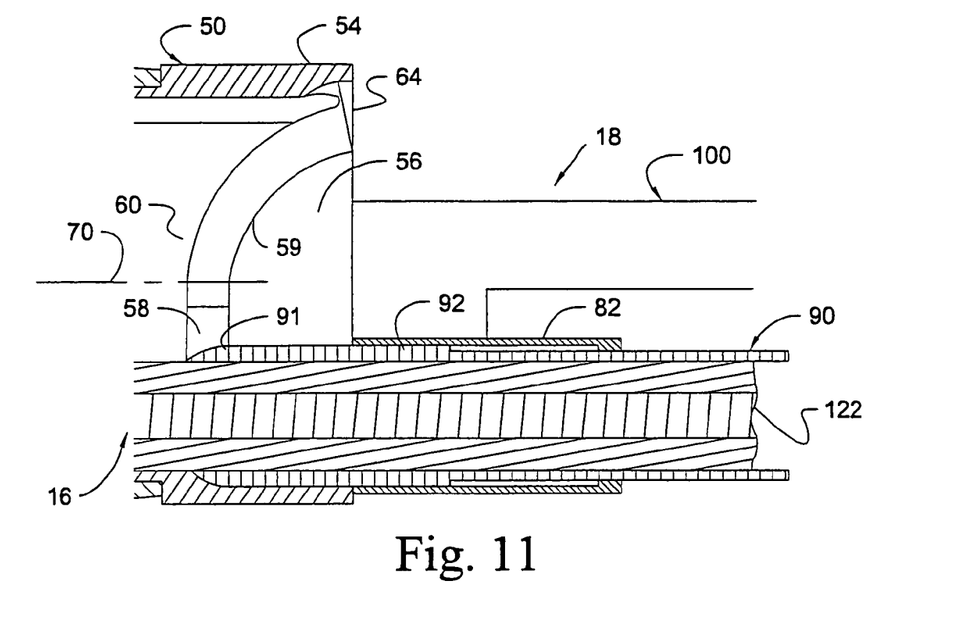
FIG. 11 is an enlarged view of a portion of the milling instrument assembly of FIG. 9.
Figure 12:
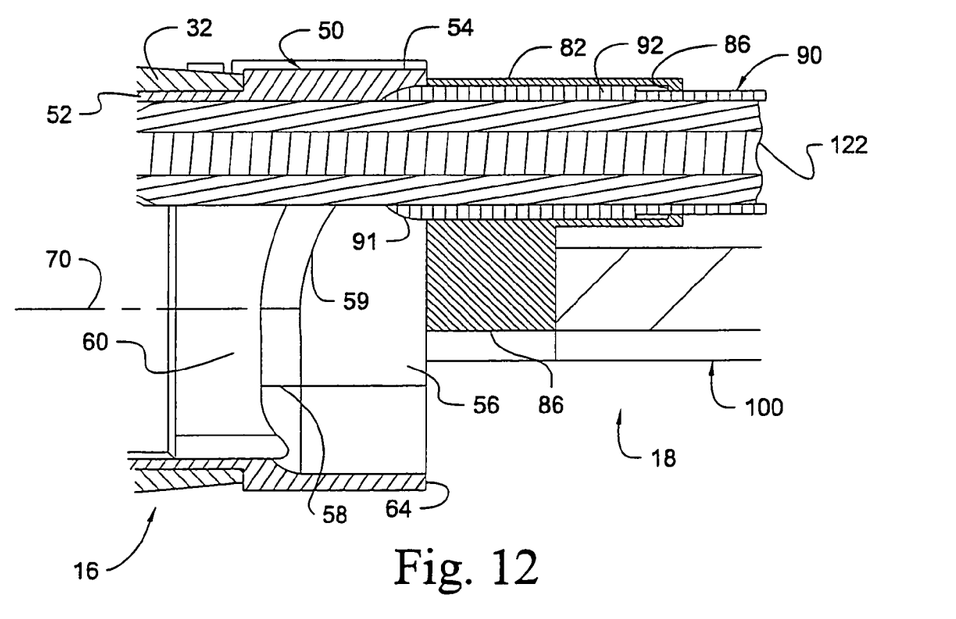
FIG. 12 is an enlarged view of a portion of the milling instrument assembly of FIG. 10.
Figures 13, 14:
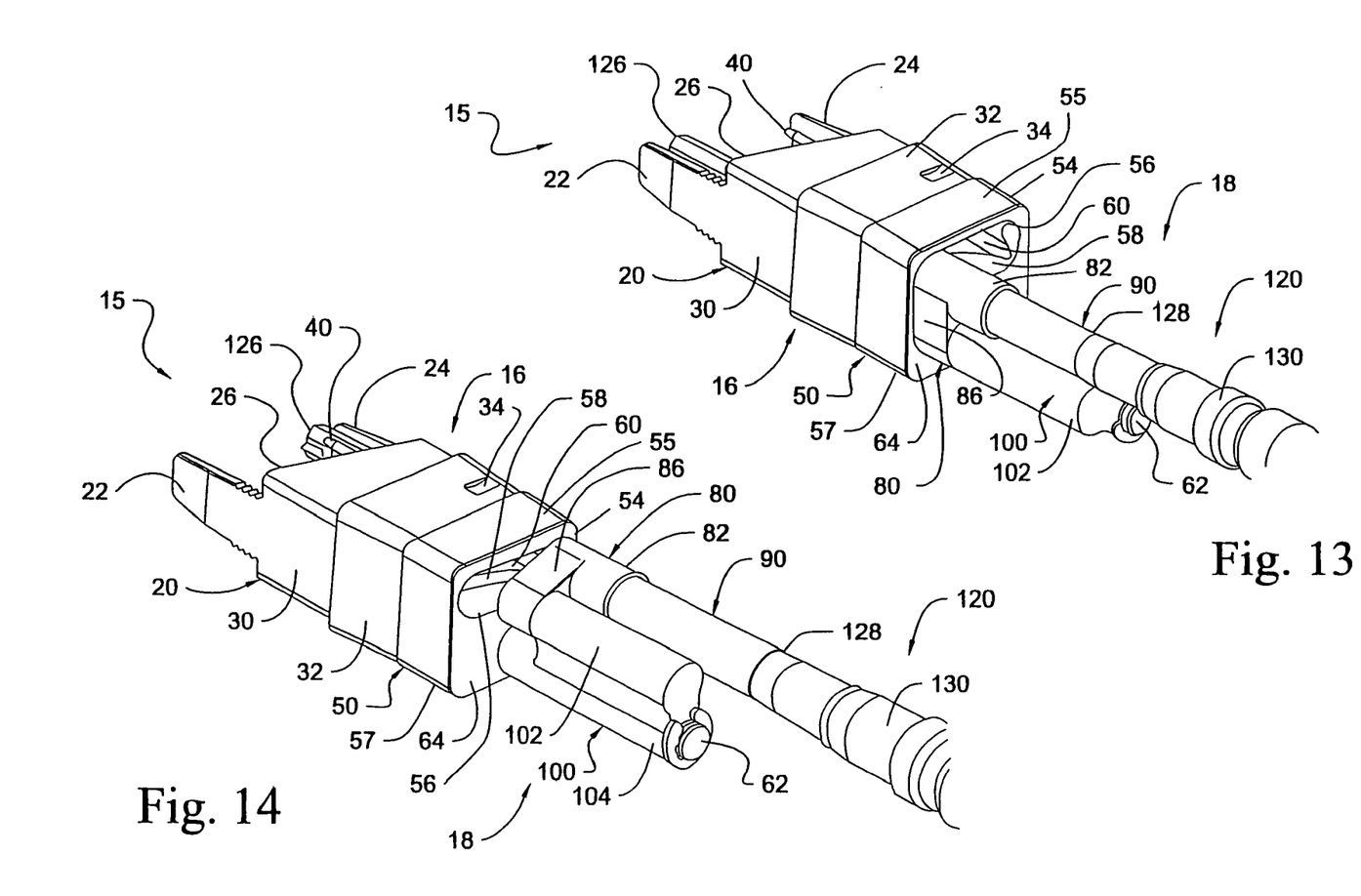
FIG. 13 is a perspective view showing the milling instrument assembly of FIG. 6 with the cutting assembly in the first position.
FIG. 14 is a perspective view showing the milling instrument assembly of FIG. 6 with the cutting assembly in the second position.

As shown in FIGS. 9-12, cutting path 180 extends parallel to guide surface 58 so that cutting element 126 is guided along cutting path 180 obliquely to longitudinal axis 70 of milling instrument assembly 15. Distal end 91 of depth tube 90 abuts guide surface 58 at the first side of slot 56, as shown in FIGS. 9, 11 and 13, where cutting element 126 extends along extension 22. Depth tube 90 and guide tube 82 are movable transversely to longitudinal axis 70 along guide surface 58 in slot 56 to position cutting element 126 of cutting assembly 120 adjacent extension 24, as shown in FIGS. 10, 12 and 14. Depth tube 90 and guide tube 82 can also be moved in the opposite direction from second extension 24 to first extension 22 while cutting with cutting element 126. The distal depth of cut can correspond to the depth extensions 22, 24 extend into the disc space.

At least a portion 59 of guide surface 58 extends proximally within slot 56 relative to the remaining portion of guide surface 58 such that portion 59 is obliquely oriented relative to longitudinal axis 70. In the illustrated embodiment, oblique portion 59 of guide surface 58 defines a curved or arcuate path that is followed by cutting path 180. Other embodiments contemplate linear paths, or combined linear and arcuate paths along the oblique portion 59 of guide surface 58. The oblique portion 59 moves cutting assembly 120 and depth tube 90 proximally in slot 56 as they move together toward second extension 24. Depth tube 90 and cutting assembly 120 also move proximally in guide tube 82 as they move together toward second extension 24. This directs cutting element 126 and thus cutting path 180 proximally in the disc space and away from the spinal canal and posterior elements of the vertebra as discussed above.

In the illustrated embodiment, oblique portion 59 is curved or arcuate. The oblique portion 59 can comprise about one half the length of guide surface along slot 56. It is contemplated that oblique portion 59 can range from the entire length of slot 56 to about one-eighth of the length of slot 56 or less. In another form, the oblique portion 59 comprises one-fourth to three fourths of the length of slot 56.

Housing assembly 16 and guide assembly 18 provide controlled cutting of non-angular or angular surfaces, with the cut being substantially maintained over a large lateral distance defined by, for example, slot 56. Housing assembly 16 and guide assembly 18 not only maintain the vertical angulation of the cutting instrument but also maintain the cutting instrument in a substantially fixed side-to-side range of movement between extensions 22, 24, limiting the potential for accidental penetration into tissues along the lateral extent of the disc space. Further, housing assembly 16 and guide assembly 18 limit the anterior-posterior depth of cutting element 126 as it moves from a first depth in the disc space along one side of the housing assembly to a second, lesser depth in the disc space along the other side of the housing assembly, and back.

It is contemplated that kits could be provided with blocks allowing varying incremental bone removal to provide the ability to adjust endplate preparation depths without removal of housing 20 from the disc space. Furthermore, in the illustrated embodiment, a block and guide assembly for preparation of the upper vertebral endplate has been disclosed, it being understood that a similarly configured block and guide assembly can be provided for substantially similar preparation of the lower vertebral endplate. Furthermore, in the illustrated embodiment, a block and guide assembly for preparation of the vertebral endplate from a right-handed (relative to the surgeon) anterior oblique approach has been disclosed. It is to be understood that a similarly configured block and guide assembly can be provided for substantially similar preparation of the endplate from a left-handed anterior oblique approach. It is further contemplated that the instruments can be used in direct anterior, anterior offset lateral and other approaches to the disc space in which an obliquely oriented cutting path may be desired.

In one surgical procedure, the disc space is accessed from an anterior oblique approach. Disc material can be removed, and the disc space distracted to the desired disc space height between the adjacent vertebrae. It is contemplated that housing 20 can be inserted over one or more disc space distractors already inserted in the disc space, or inserted directly into the disc space. It is further contemplated that a guide tube, such as guide tube 132 can be removably attached to the proximal end of housing 20 either before or after insertion thereof. The guide tube can have a working channel to slidingly receive the proximal end of housing 20 therein. Block 50, guide assembly 18 and cutting assembly 120 can be inserted through the guide tube for attachment with housing 20, or attached to housing 20 with guide tube removed.

After the disc space has been prepared, including removal of a desired amount of bone from the vertebral endplates at the desired angle and depth with milling instrument assembly 15, block 50, guide assembly 18 and cutting assembly 120 can be removed from housing 20. The guide tube can be reattached, if desired, to housing 20. An implant can be inserted through the guide tube and housing 20 into the prepared disc space. It is contemplated that the implant can be an interbody spacer, interbody fusion device, artificial disc or other intervertebral implant. The implant can be made from bone material or synthetic material. The housing and any attached guide tube can then be removed.

While guide surface 58 has been shown in slot 56, other locations for guide surface 58 are contemplated. For example, guide surface 58 could be formed along a projecting extending proximally from block 50, along the proximal face 64 of block 50, or in housing 20.

While the invention has been illustrated and described in detail in the drawings and foregoing description, the same is to be considered as illustrative and not restrictive in character, it being understood that all changes and modifications that come within the spirit of the invention are desired to be protected.

What is claimed is:

1. A method for preparing endplates of adjacent vertebrae for insertion of an implant in a disc space between the adjacent vertebrae, comprising:
    accessing the disc space through a housing assembly that extends along an axis that extends generally in an anterior oblique direction relative to a sagittal plane of the adjacent vertebrae;
    positioning a cutting instrument that extends along a longitudinal axis through a depth tube with a distal end of the depth tube in contact with a guide surface recessed in a proximal face of the housing assembly and the guide surface extends along a slot that extends through the housing assembly, the cutting instrument further extending distally from the depth tube through the slot and into the disc space;
    linking the depth tube to the housing assembly with a guide member; and
    milling at least one endplate in side-to-side movement along a cutting path defined by the guide surface with the guide surface having at least a portion obliquely oriented to the longitudinal axis so that the obliquely oriented portion extends proximally toward the proximal face of the housing assembly as it approaches one side of the housing assembly, wherein as the guide member moves along the proximal face of the housing assembly the depth tube moves along the obliquely oriented portion of the guide surface and proximally relative to the guide member to direct the cutting instrument proximally in the disc space along a portion of the cutting path obliquely oriented to the longitudinal axis.

2. The method of claim 1, wherein the cutting path and the guide surface each include a portion orthogonally oriented to the longitudinal axis.

3. The method of claim 1, wherein the portion of the cutting path and the portion of the guide surface obliquely oriented to the longitudinal axis are arcuate.

4. The method of claim 1, further comprising distracting the adjacent vertebrae.

5. The method of claim 1, further comprising inserting an implant in the disc space.

6. The method of claim 1, further comprising cutting a surface on the at least one endplate in an oblique angle to an axial plane of the adjacent vertebrae.

7. A method for preparing an endplate of a vertebra of a spinal column, comprising:
   positioning a housing assembly adjacent the vertebra in an anterior oblique approach with a cutting assembly extending along an axis through the housing assembly linking the cutting assembly and the housing assembly with a guide assembly;
   guiding the cutting assembly from a first side of the housing assembly to an opposite second side of the housing assembly along a cutting path along the endplate extending transversely to the anterior oblique approach, wherein a first portion of the cutting path adjacent the first side is linear and substantially orthogonal to the axis and a second portion of the cutting path is obliquely oriented to the axis and extends proximally from the linear first portion of the cutting path in a proximal direction as it approaches the second side of the housing assembly, wherein guiding the cutting assembly includes:
   moving the cutting assembly along a guide surface formed along a slot extending through the housing assembly;
   locating the cutting assembly in a depth tube and through the slot, wherein the depth tube is positioned in a guide tube;
   moving the guide tube along a proximally oriented face of the housing assembly while moving the depth tube in abutting engagement with and along the guide surface; and
   axially moving the depth tube relative to the guide tube while moving the guide tube along the proximally oriented face and while moving the depth tube along the guide surface to follow the guide surface with the depth tube along the obliquely oriented second portion of the cutting path.

8. The method of claim 7, wherein the second portion of the cutting path extends along a curve.

9. The method of claim 7, further comprising:
   pivotally linking the cutting assembly and the housing assembly with the guide assembly.

10. The method of claim 9, wherein the slot includes a through-way and the guide surface extends about the through-way.

11. A method for preparing an endplate of a vertebra of a spinal column, comprising:
   positioning a housing assembly adjacent the vertebra in an anterior oblique approach, the housing assembly including a slot extending therethrough between a distal side of the housing assembly located toward the vertebra and a proximal side of the housing assembly located away from the vertebra and a cutting assembly through the slot and adjacent the endplate;
   linking the cutting assembly to the housing assembly with a guide assembly;
   moving the cutting assembly along the slot and the endplate with the guide assembly, wherein moving the cutting assembly includes moving the cutting assembly along a linear path portion from a first side of the housing assembly toward a second side of the housing assembly and moving the cutting assembly from the linear path portion to the second side of the housing assembly along an obliquely oriented path portion that extends obliquely to the anterior oblique approach and proximally from the linear path portion toward the proximal side of the housing assembly as the obliquely oriented path portion approaches the second side of the housing assembly, wherein moving the cutting assembly includes:
   locating the cutting assembly in a depth tube and through the slot, wherein the depth tube is positioned in a guide tube;
   moving the guide tube along a proximally oriented face of the housing assembly while moving the depth tube in abutting engagement with a guide surface extending along the slot; and
   axially moving the depth tube relative to the guide tube to follow the guide surface with the depth tube along the obliquely oriented path portion.

12. The method of claim 11, wherein the linear path portion is orthogonal to the anterior oblique approach.

13. The method of claim 12, wherein the obliquely oriented portion of the cutting path is arcuate.

14. The method of claim 11, wherein the obliquely oriented path portion of the cutting path is arcuate.

15. The method of claim 11, wherein the slot is oriented so that the cutting assembly forms a surface on the endplate of the vertebra that is obliquely angled to an axial plane of the spinal column when moving the cutting assembly along the slot.

* * * * *